United States Patent [19]

Cunningham

[11] 4,318,404
[45] Mar. 9, 1982

[54] APPLICATOR AND TAMPON

[76] Inventor: Thomas W. Cunningham, 3580 Emerywood La., Orlando, Fla. 32806

[21] Appl. No.: 43,231

[22] Filed: May 29, 1979

[51] Int. Cl.³ ............................................. A61F 15/00
[52] U.S. Cl. ................................................... 128/263
[58] Field of Search ................ 128/262, 263, 270, 285

[56] References Cited

U.S. PATENT DOCUMENTS

| 2,401,585 | 6/1946 | Seidler | 128/263 |
| 2,413,480 | 12/1946 | Winter | 128/263 |
| 3,358,686 | 12/1967 | Asaka | 128/263 |
| 3,499,447 | 3/1970 | Mattes et al. | 128/263 |
| 3,749,093 | 7/1973 | Bloom | 128/263 |

FOREIGN PATENT DOCUMENTS 2406823  8/1975  Fed. Rep. of Germany ...... 128/262

*Primary Examiner*—C. Fred Rosenbaum

[57] ABSTRACT

An applicator for a member having a surface, such as a tampon, includes a flexible applicator along the surface with the applicator having a convolution so as to double the applicator upon itself to form parallel walls with the convolution there between. The surface of the member may be exposed by relative movement of one of the walls of the applicator with respect to the member.

16 Claims, 3 Drawing Figures

APPLICATOR AND TAMPON

BACKGROUND OF THE INVENTION

1. Field of the Invention

The present invention relates to applicators.

2. Description of the Prior Art

During the menstruation cycle, women customarily insert an oblong porous object customarily referred to as a tampon into the vagina to absorb discharge fluids from the body. During the insertion process, the body muscles tend to contract, thus making entry of the tampon uncomfortable.

There have been numerous tampon wrappings and applicators devised in the prior art to attempt to avoid this discomfort.

In U.S. Pat. No. 3,749,093, Bloom discloses an insertable device package for tampons, in which the insertion device comprises an elongated sheath having a pair of side walls separated by a convolution, the tampon being inserted by pushing along the bottom thereof to force the tampon through one end, causing the convolution to roll inwardly, extending the inner sidewall during the insertion process.

In U.S. Pat. No. 2,922,422, Bletzinger discloses a cellulose outer shell as an applicator for a tampon. Similar arrangements are disclosed in U.S. Pat. Nos. 2,922,423 to Richard, et al, and 3,499,447 to Mattes, et al.

Crockford, in U.S. Pat. Nos. 3,058,469, and Kobler, et al, in 3,135,262 both disclose a protective sheath that may be folded back during insertion of the tampon. Asaka, in U.S. Pat. No. 3,358,636, discloses an insertion mechanism.

Other prior art of interest includes U.S. Pat. No. 3,068,867 to Bletzinger, et al, which discloses the use of an insertion rod and a withdrawal string.

SUMMARY OF THE INVENTION

The present invention contemplates an applicator for a member comprising the member having a surface, with a flexible applicator along the surface and having a convolution so as to double the applicator upon itself to form parallel walls with the convolution there between. The surface of the member may be exposed by relative movement of one of the walls of the applicator with respect to the member. In a specific arrangement, the member is enclosed inside a flexible applicator sleeve with the convolution along the sleeve, permitting the sleeve to be rolled along a direction substantially parallel with a central axis of the member.

A preferred embodiment of the present invention contemplates an applicator and tampon, in which the tampon is formed of an oblong absorbent member having a central axis and a forward end adapted to be extended first into the vagina. A flexible applicator sleeve is fitted about the tampon and overlapping a portion of the forward end of the tampon, with a convolution along the sleeve permitting the sleeve to be rolled along a direction substantially parallel with the central axis during or after movement of the tampon into the vagina. For these purposes, the term "convolution" means a single roll, with a portion of the sleeve about another portion of the sleeve.

In a preferred embodiment of the present invention, the flexible sleeve is formed of two substantially parallel walls separated by the convolution, with the convolution being adjacent to forward end of the tampon, the convolution forming an opening at that forward end.

THE DRAWING

FIGS. 1, 2 and 3 illustrate consecutive steps in the use of the applicator of the present invention with a tampon.

DETAILED DESCRIPTION OF THE PREFERRED EMBODIMENT

Figure 1:
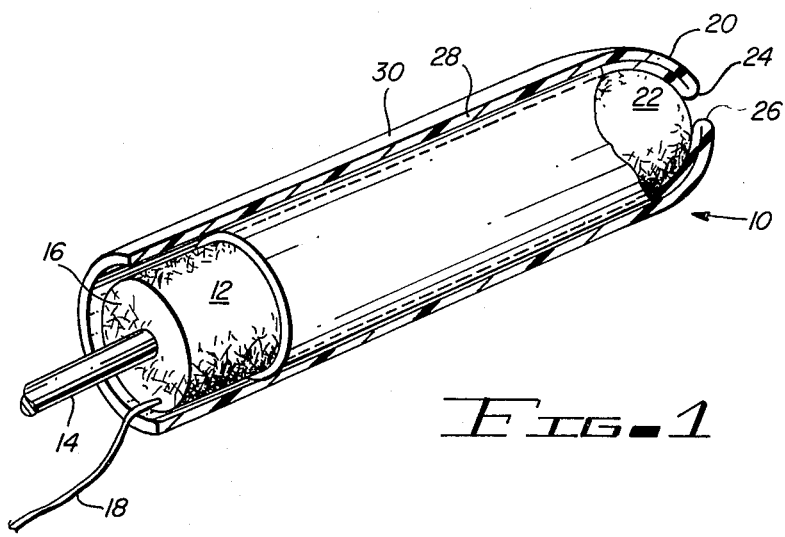

An applicator and tampon in accordance with the present invention and its manner of intended use will now be described with reference to FIGS. 1, 2 and 3.

The applicator and tampon, referred to generally by the reference numeral 10, includes a tampon 12 comprising an absorbent fiber body, which is compressed to such an extent that it is substantially stable under normal atmospheric conditions but expands when wetted during its intended use. The tampon 12 is provided with a conventional insertion rod 14 which may comprise wood, paper or any other material of a suitable nature, and which is appropriately joined at the distal end 16 of the tampon 12. The applicator and tampon is further provided with a conventional withdrawal string 18 suitably anchored to the tampon 12 and exists adjacent to the distal end 16.

The applicator, referred to generally by the reference numeral 20, comprises a flexible sleeve about the tampon and overlapping a portion of the forward end 22 of the tampon 12. A suitable material for use as the sleeve 20 may be, for example, polyethylene or polypropylene or other material having sufficient flexibility to form the desired convolution.

The sleeve 20 is wrapped about the tampon 12 in such a manner as to form a convolution 24 toward the forward end 22 of the tampon 12, the convolution forming an opening 26 axial with the central axis of the tampon 12 and overlapping the forward end 22. The convolution 24 thus separates the sleeve 20 into two sidewalls 28 and 30, the first sidewall 28 being next adjacent to the tampon 12, and the outer sidewall 30 being next adjacent to the first wall 28.

The manner in which the applicator and tampon 10 is employed will now be described with reference to FIGS. 2 and 3.

Figure 2:
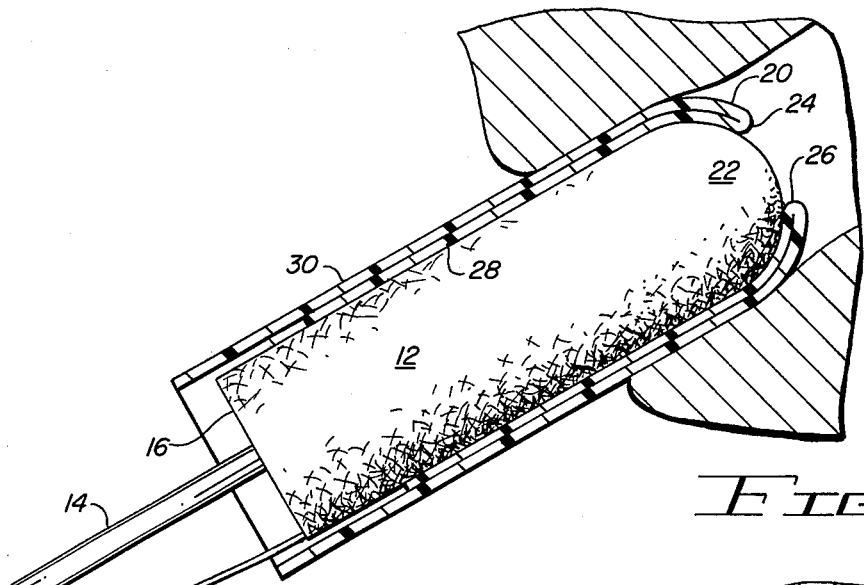
Figure 3:
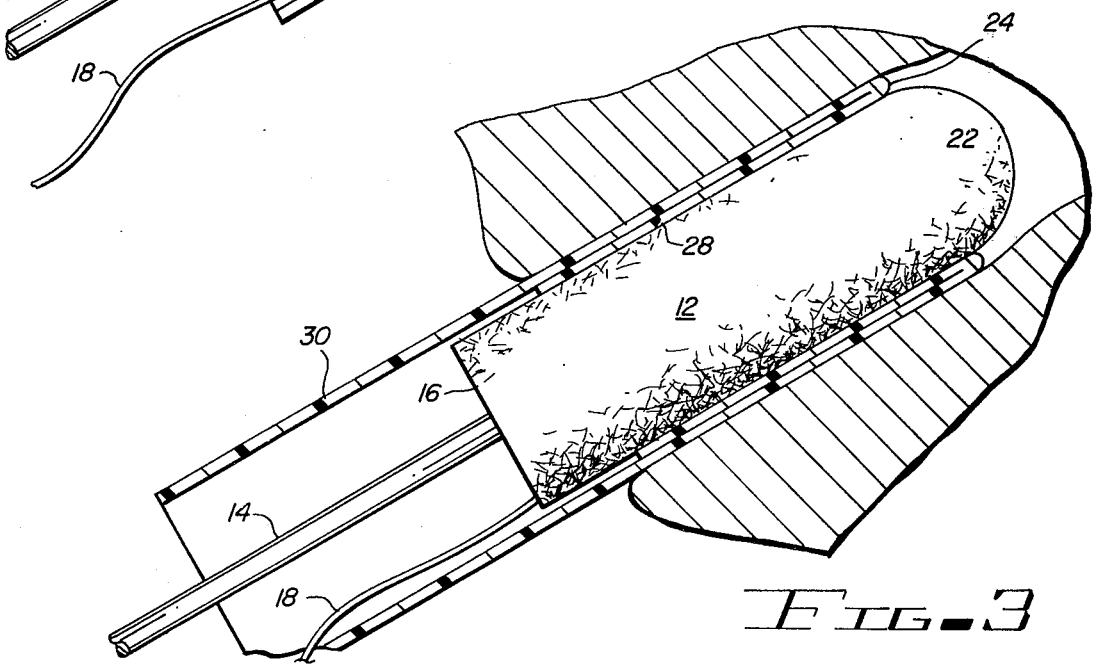

Noting FIG. 2, the applicator and tampon 10 are inserted into the vagina, with the muscle tissue coming in contact with the outer wall 30 of the sleeve 20. As the tampon 12 is forced into the vagina by application of pressure on the insertion rod 14, the sleeve 20 rolls at the convolution 24, with the outer wall 30 remaining substantially stationary. After the tampon is inserted in the desired manner, the insertion rod 14 may be removed in a conventional fashion by rotation thereof, and the sleeve 20 may be removed by simply pulling the outer extremity of the outside wall 30 away from the vagina. Alternatively, the tampon 12 is placed into position and the sleeve 20 is removed while the tampon remains relatively stationary. It will thus be seen that a tampon and applicator constructed in accordance with the present invention reduces significantly the amount of tampon insertion discomfort. Further, the use of the thin poly-resin sleeve 20 provides relatively easy entry during the insertion process.

It will be understood that the sleeve 20 may be coated with an appropriate lubricant. It will be further understood that the sleeve 20 may be adapted for use with tampons of different sizes and configurations, i.e., rectangular or other shapes.

While the applicator has been described above for use with tampons, it will be understood that the applicator may be employed with other products as well.

I claim:

1. An applicator for a member comprising:
   a member having a surface;
   a flexible applicator along said surface, said applicator having a convolution so as to double said applicator upon itself to form parallel walls each lying in contact with the other, and with said convolution therebetween, the outside wall having a sufficient length to extend along said member from said convolution to the end of said member opposite said convolution; and wherein
   said surface of said member may be exposed by grasping said outside wall at said opposite end of said member, and a relative movement of said outside wall of said applicator with respect to said member, causing said applicator to roll at said convolution.

2. The applicator recited in claim 1 wherein said flexible applicator comprises a non-absorbent material.

3. The applicator recited in claims 1 or 2 wherein said flexible applicator comprises a layer of poly-resin material.

4. An applicator and tampon comprising:
   a tampon formed of an oblong absorbent member having a central axis and a forward end adapted to be inserted first into the vagina;
   a flexible applicator sleeve about said tampon; and
   a convolution along said sleeve and tampon, said sleeve having a sufficient length permitting said sleeve to be folded into contact with itself and to extend to the rearward end of said tampon opposite said forward end, whereby said sleeve may be rolled along a direction substantially parallel with said central axis of the tampon by grasping the outside of said sleeve, said convolution forming an opening at the forward end of said tampon, said tampon moving through said opening during said rolling of said sleeve.

5. The applicator and tampon recited in claim 4 wherein said flexible sleeve comprises a non-absorbent material.

6. The applicator and tampon recited in claims 4 or 2 wherein said flexible sleeve comprises a layer of a poly-resin material.

7. The applicator and tampon recited in claim 4 wherein said flexible sleeve is formed of two substantially parallel walls separated by said convolution.

8. The applicator and tampon recited in claim 7 wherein said convolution is adjacent said forward end of said tampon.

9. The applicator and tampon recited in claim 8 wherein said convolution forms an opening at said forward end.

10. The applicator and tampon recited in claim 4 further comprising an insertion rod joined with the distal end of said tampon.

11. The applicator and tampon recited in claim 4 further comprising a withdrawal string joined to said tampon adjacent the distal end thereof.

12. An applicator and tampon as recited in claim 4, wherein said flexible applicator sleeve overlaps a portion of said forward end of said tampon.

13. An applicator and tampon comprising:
    a tampon formed of an oblong absorbent member having a central axis and a forward end adapted to be extended first into the vagina;
    a non-absorbent, flexible applicator sleeve formed of a first wall surrounding and next adjacent to the periphery of said tampon and a second wall surrounding and next adjacent said first wall, said first and second walls being substantially parallel and said sleeve further including a convolution between said first and second walls;
    said sleeve overlapping a portion of the forward end of said tampon and forming an opening adjacent said forward end of said tampon in the direction of extension into the vagina, said second wall having a lengthwise dimension to extend substantially to the rearward end of said tampon; and wherein
    upon insertion of said tampon and applicator into the vagina, said second wall comes into frictional contact with the walls of the vagina to permit a relatively comfortable insertion of said tampon, while the rolling of said sleeve permits a comfortable removal of said sleeve by grasping said second wall adjacent said rearward end and effectuating relative motion between said second wall and said tampon.

14. An applicator and tampon recited in claims 7 or 13 wherein said first wall reduces in lengthwise dimension and said second wall increases in lengthwise dimension, as said sleeve is rolled at said convolution.

15. The applicator and tampon recited in claim 13 further comprising an insertion rod extending into the distal end of said tampon and a drawstring exiting said tampon adjacent said distal end.

16. An applicator and tampon comprising:
    a tampon formed of an oblong absorbent member having a central axis and a forward end adapted to be extended first into the vagina:
    a non-absorbent, flexible applicator sleeve formed of a first wall surrounding and next adjacent to the periphery of said tampon and a second wall surrounding and next adjacent said first wall, said first and second walls lying in contact with each other and being substantially parallel, and second wall having a length sufficient to extend adjacent to the rearward end of said tampon, and said sleeve further including a convolution connected to, and between said first and second walls;
    said sleeve overlapping a portion of the forward end of said tampon and forming an opening adjacent said forward end of said tampon in the direction of extension into the vagina; and wherein
    upon insertion of said tampon and applicator into the vagina, said second wall comes into frictional contact with the walls of the vagina to permit a relatively comfortable insertion of said tampon, while the rolling of said sleeve by grasping said second wall at the rearward end of said tampon followed by relative motion between said second wall and said tampon permits a comfortable removal of said sleeve.

* * * * *